US009642965B2

(12) United States Patent
Marshall et al.

(10) Patent No.: US 9,642,965 B2
(45) Date of Patent: May 9, 2017

(54) INFUSION PUMP CASSETTE AND CASSETTE INTERFACE CONFIGURED TO ASSIST CASSETTE REMOVAL

(71) Applicant: Zevex, Inc., Salt Lake City, UT (US)

(72) Inventors: Michael A. Marshall, Herriman, UT (US); Jeffery T. Juretich, Herriman, UT (US)

(73) Assignee: Zevex, Inc., Salt Lake City, UT (US)

( * ) Notice: Subject to any disclaimer, the term of this patent is extended or adjusted under 35 U.S.C. 154(b) by 0 days.

(21) Appl. No.: 15/026,444

(22) PCT Filed: Jul. 17, 2015

(86) PCT No.: PCT/US2015/040858
§ 371 (c)(1),
(2) Date: Mar. 31, 2016

(87) PCT Pub. No.: WO2016/093890
PCT Pub. Date: Jun. 16, 2016

(65) Prior Publication Data
US 2016/0331891 A1    Nov. 17, 2016

Related U.S. Application Data

(60) Provisional application No. 62/090,963, filed on Dec. 12, 2014.

(51) Int. Cl.
*F04B 43/00*    (2006.01)
*A61M 5/142*    (2006.01)
(Continued)

(52) U.S. Cl.
CPC ........ *A61M 5/142* (2013.01); *A61M 5/14228* (2013.01); *A61M 5/14232* (2013.01);
(Continued)

(58) Field of Classification Search
CPC .......... F04B 43/08; F04B 43/12; A61M 5/142
(Continued)

(56) References Cited

U.S. PATENT DOCUMENTS 5,927,956 A * 7/1999 Lim .................... F04B 43/1253
                                                   417/477.13
6,494,694 B2   12/2002 Lawless et al.
(Continued)

FOREIGN PATENT DOCUMENTS

EP    2169225    3/2010
WO    0123277    4/2001
(Continued)

*Primary Examiner* — Charles Freay
*Assistant Examiner* — Christopher Bobish
(74) *Attorney, Agent, or Firm* — Hodgson Russ LLP

(57) ABSTRACT

A cassette apparatus for an infusion pump includes a cassette for operatively connecting administration set tubing to the infusion pump and a cassette interface a cassette interface on the infusion pump for removably receiving the cassette. The cassette includes a press tab having an upwardly facing press surface and an undersurface, and the cassette interface includes at least one fulcrum member, wherein the undersurface of the press tab engages the fulcrum member(s) when the cassette is received by the cassette interface. As a result, the cassette is pivotable relative to fulcrum member(s) by pressing the press surface of the press tab to assist in removing the cassette from the cassette interface.

5 Claims, 4 Drawing Sheets

(51) Int. Cl.
*F04B 43/08* (2006.01)
*F04B 43/12* (2006.01)
*A61M 39/12* (2006.01)

(52) U.S. Cl.
CPC .............. *A61M 39/12* (2013.01); *F04B 43/08* (2013.01); *F04B 43/12* (2013.01); *A61M 2205/12* (2013.01); *A61M 2205/121* (2013.01)

(58) Field of Classification Search
USPC ...................................................... 417/477.2
See application file for complete search history.

(56) References Cited

U.S. PATENT DOCUMENTS

| | | |
|---|---|---|
| 6,659,976 B2 | 12/2003 | Beck et al. |
| 7,070,575 B2 | 7/2006 | Beck et al. |
| 7,632,079 B2 * | 12/2009 | Hershberger .... A61B 17/32002 417/477.2 |
| 7,758,324 B2 * | 7/2010 | Baumann ............ F04B 43/1253 417/474 |
| 8,377,001 B2 | 2/2013 | Pfouts et al. |
| 8,425,470 B2 | 4/2013 | Beck et al. |
| 8,459,968 B2 * | 6/2013 | Juretich ............... F04B 43/1261 417/477.2 |
| 8,486,020 B2 | 7/2013 | Hills et al. |
| 8,491,285 B2 | 7/2013 | Haser et al. |
| 8,734,138 B2 * | 5/2014 | Baumann ............ F04B 43/1253 417/474 |
| 2002/0151838 A1 | 10/2002 | Beck |
| 2009/0053085 A1 | 2/2009 | Thompson |
| 2012/0294743 A1 * | 11/2012 | Ono ..................... F04B 43/1276 417/477.2 |
| 2014/0135731 A1 | 5/2014 | Breitweiser et al. |
| 2016/0296369 A1 * | 10/2016 | Ross .................. A61M 1/0058 |

FOREIGN PATENT DOCUMENTS

| | | |
|---|---|---|
| WO | 2012044807 | 4/2012 |
| WO | 2014062403 | 4/2014 |

* cited by examiner

INFUSION PUMP CASSETTE AND CASSETTE INTERFACE CONFIGURED TO ASSIST CASSETTE REMOVAL

FIELD OF THE INVENTION

The present invention relates generally to infusion pumps for controlled delivery of liquid food and medications to patients. More specifically, the present invention relates to a removable cassette apparatus by which an administration tubing set is operatively connected to an infusion pump, wherein the cassette apparatus is configured to assist a user in removing the cassette from the pump.

BACKGROUND OF THE INVENTION

Programmable infusion pumps are used to carry out controlled delivery of liquid food for enteral feeding and medications for various purposes, for example pain management. In a common arrangement, an infusion pump receives a disposable administration set comprising a cassette removably received by the pump and flexible tubing connected to the cassette for providing a fluid delivery path through the pump.

The administration set may include a pumping segment of tubing that wraps around a rotor mechanism of the pump, and the cassette may include a pair of tubing connectors to which opposite ends of the tubing segment are connected. The rotor mechanism may have pinch rollers or fingers that deform the tubing segment as the rotor rotates to progressively urge fluid through the tubing in a peristaltic manner. The cassette may have another pair of tubing connectors for connecting inflow tubing carrying fluid from a fluid source and outflow tubing leading to a patient. As a result, a flow path is provided from the inflow tubing, through the tubing segment, to the outflow tubing.

The pump may have a cassette interface configured to provide a nesting region for receiving the cassette when it is loaded into the pump. In prior art designs, such as that shown in U.S. Pat. No. 7,070,575, the cassette interface defines a shaped recess into which the cassette fits when the cassette is loaded in the pump. As a result, some users have difficulty removing the cassette and administration set tubing from the pump after use.

What is needed is a cassette and a corresponding cassette interface that facilitate removal of the cassette and administration set tubing from the pump.

SUMMARY OF THE INVENTION

A cassette apparatus for an infusion pump is configured so that a user may load and remove the cassette quickly and easily. The cassette apparatus generally comprises a cassette for operatively connecting administration set tubing to the infusion pump, and a cassette interface on the infusion pump for removably receiving the cassette.

In accordance with the present invention, the cassette includes a press tab having an upwardly facing press surface and an undersurface, and the cassette interface includes at least one fulcrum member, wherein the undersurface of the press tab engages the at least one fulcrum member when the cassette is received by the cassette interface. As a result, the cassette is pivotable relative to the at least one fulcrum member by pressing the press surface of the press tab to assist in removing the cassette from the cassette interface.

In one embodiment of the invention, the cassette includes a vertical rib extending downwardly from the undersurface of the press tab, and the cassette interface includes a pair of fulcrum members laterally spaced from one another to define a slot therebetween. When the cassette is loaded, the vertical rib of the cassette is received in the slot of the cassette interface between the pair of fulcrum members, and the undersurface of the press tab engages each of the pair of fulcrum members, such that the cassette is pivotable relative to the pair of fulcrum members by pressing the press surface of the press tab.

The cassette may also include an inflow tubing connector, an outflow tubing connector, an upstream pumping segment connector in flow communication with the inflow tubing connector, and a downstream pumping segment connector in flow communication with the outflow tubing connector. The downstream pumping segment connector may include an in-line occluder for restricting flow through the downstream pumping segment connector.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
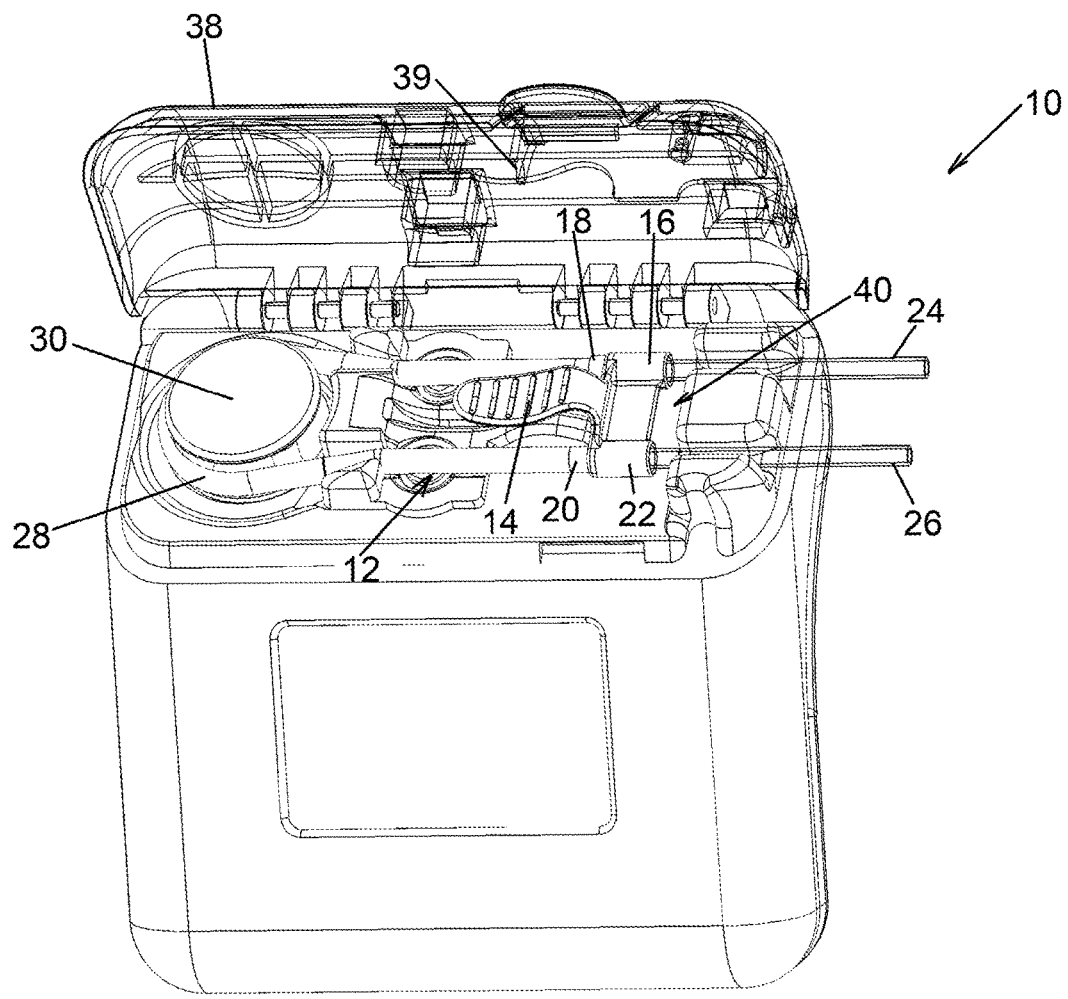
FIG. 1 is perspective view of an infusion pump and cassette embodying a cassette apparatus formed in accordance with an embodiment of the present invention.
Figure 2:
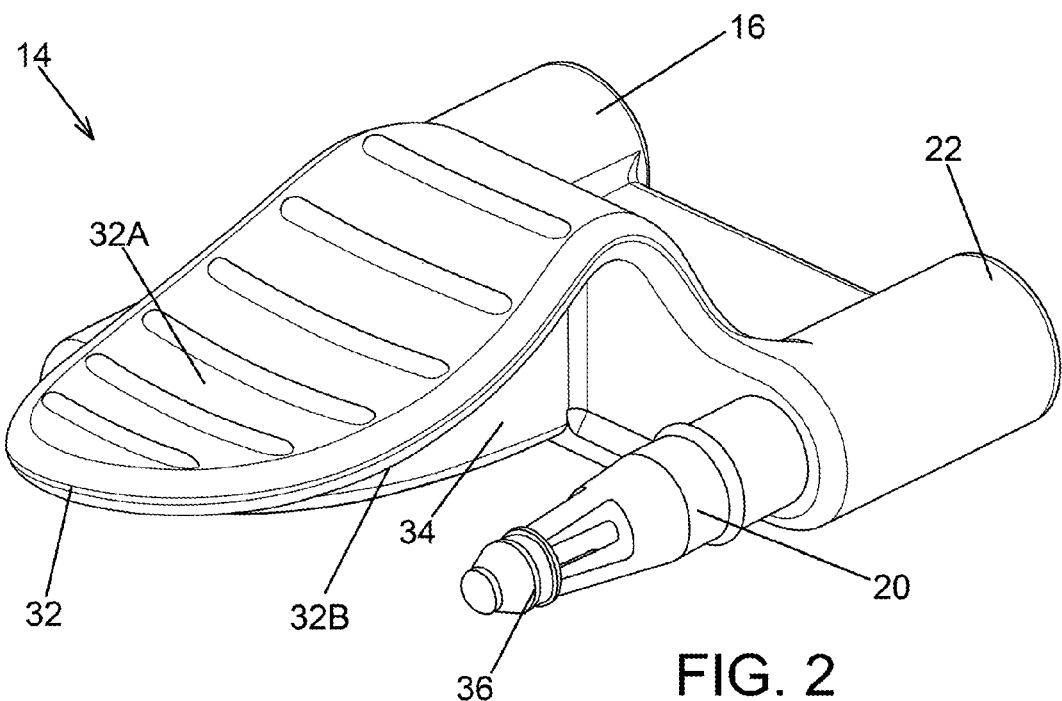
FIG. 2 is a perspective view of the cassette shown in FIG. 1, taken generally from above the cassette.
Figure 3:
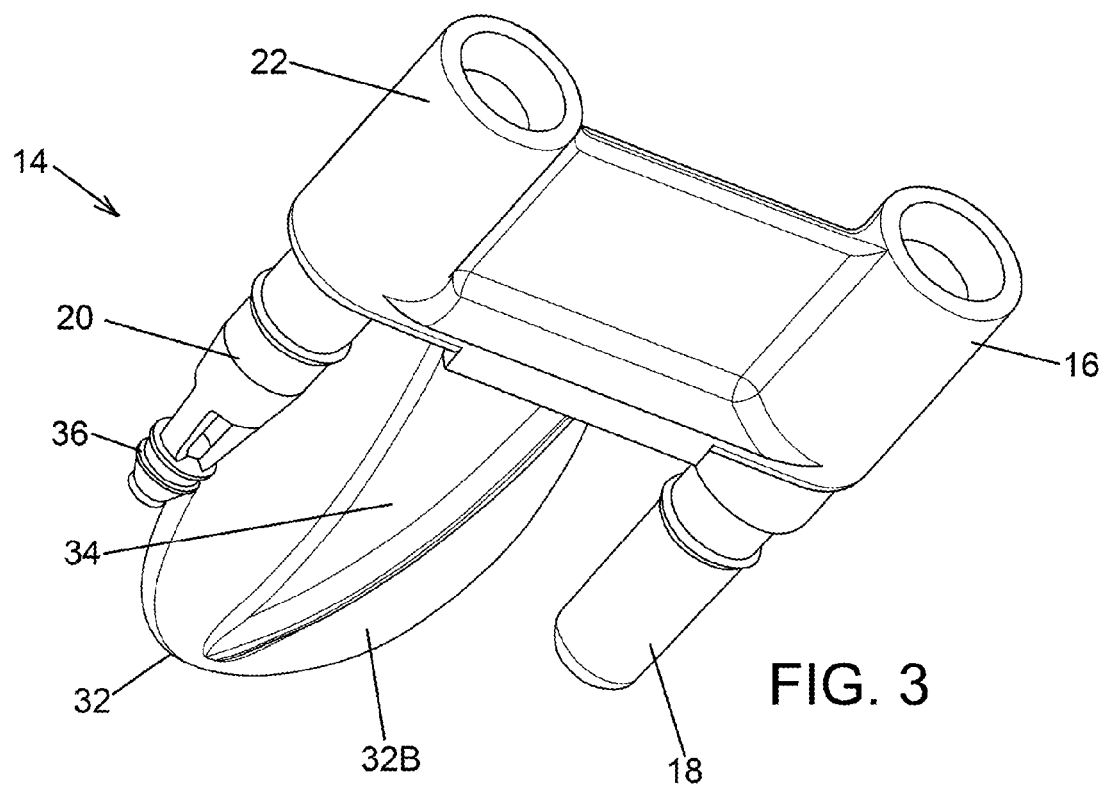
FIG. 3 is another perspective view of the cassette shown in FIG. 1, taken generally from below the cassette.

FIG. 1 shows an infusion pump 10 in which an administration set 12 is removably received. Administration set 12 includes a cassette 14, which is shown by itself in FIGS. 2 and 3. Cassette 14 may include an inflow connector 16, an upstream pumping segment connector 18 in flow communication with inflow connector 16, a downstream pumping segment connector 20, and an outflow connector 22 in flow communication with downstream pumping segment connector 20. Administration set 12 may further include inflow tubing 24 having one end mated to inflow connector 16 and an opposite end (not shown) connected to a fluid source, and outflow tubing 26 having one end connected to outflow connector 22 and an opposite end (not shown) connected to a patient. Finally, administration set 14 may further include a pumping segment of tubing 28 having one end mated to upstream pumping segment connector 18 and an opposite end mated to downstream pumping segment connector 20.

In the illustrated embodiment, pump 10 is a rotary peristaltic pump having a rotor 30, wherein pumping segment 28 is wrapped around rotor 30 and is engaged by angularly spaced rollers on rotor 30 as the rotor rotates to provide peristaltic pumping action forcing liquid through the tubing of administration set 12. As may be understood by reference to FIG. 1, when rotor 30 rotates in a counter-clockwise direction, liquid is moved from inflow tubing 24 through inflow connector 16 and upstream pumping segment connector 18 to pumping segment 28, and then from pumping segment 28 through downstream pumping segment connector 20 and outflow connector 22 to outflow tubing 26. Although the present invention is described in the context of a rotary peristaltic pump, the invention is not limited to this type of infusion pump. The invention may be practiced with any type of infusion pump that receives an administration set having a cassette.

Cassette 14 also includes a press tab 32 having an upwardly facing press surface 32A and an undersurface 32B. Cassette 14 may further include a vertical rib 34 extending downwardly from undersurface 32B. In a particular embodiment, cassette 14 may include an in-line occluder 36 which may be incorporated into downstream pumping segment connector 20. In-line occluder 36 prevents flow when pump door 38 is open. An actuator 39 on an underside of pump door 38 engages pumping segment 28 in a manner which opens a flow path around occluder 36 when door 38 is closed.

Figure 4:
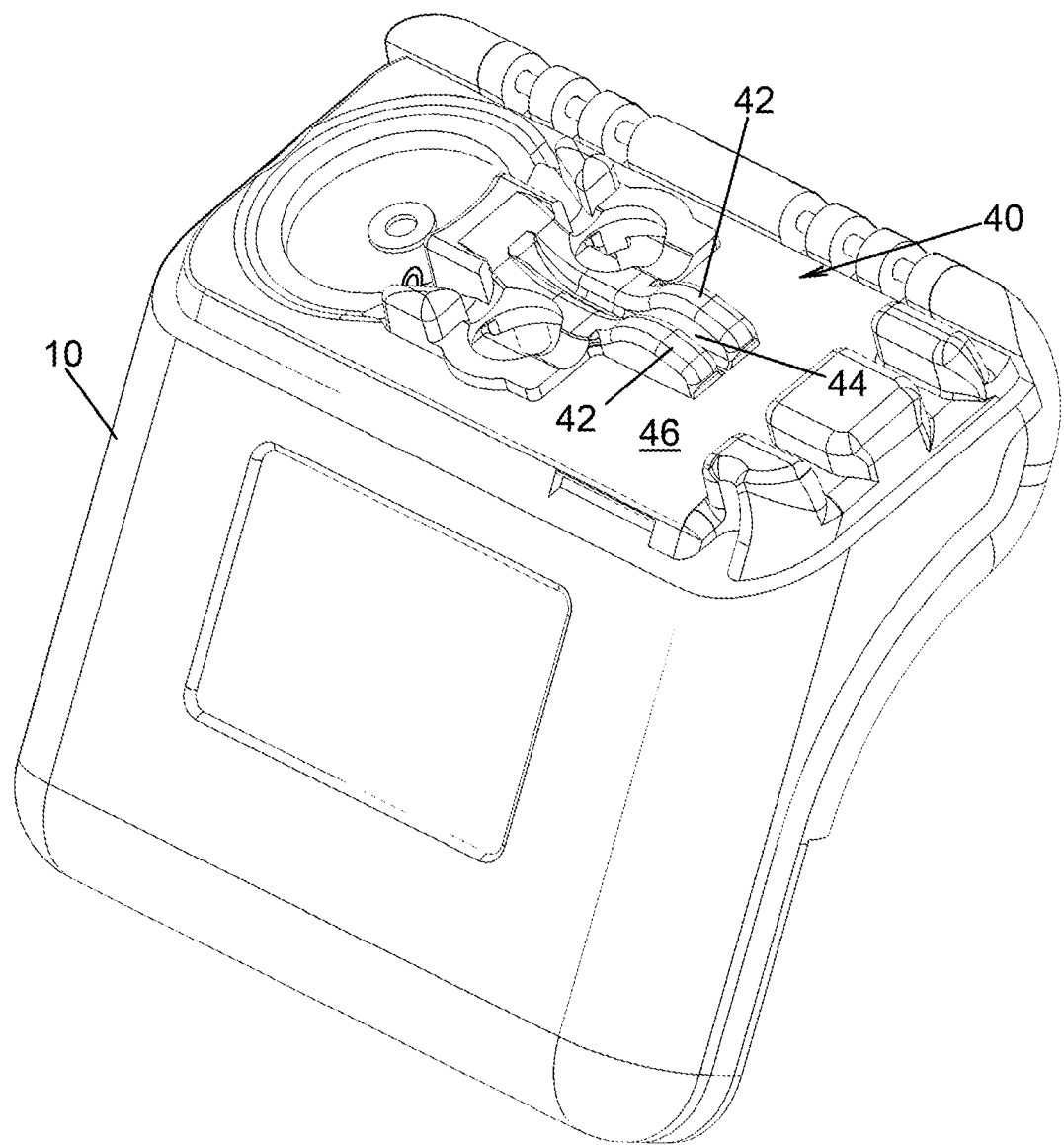
FIG. 4 is a perspective view of a cassette interface of the infusion pump shown in FIG. 1.

As seen in FIG. 1, infusion pump 10 includes a cassette interface 40 for removably receiving cassette 14. FIG. 4 shows cassette interface 40 without a loaded administration set. In the illustrated embodiment, cassette interface 40 includes a pair of fulcrum members 42 laterally spaced from one another to define a slot 44 therebetween. Fulcrum members 42 extend upward from a base surface 46 of the cassette interface. Cassette 14 and cassette interface 40 may be formed of molded plastic.

Figure 5:
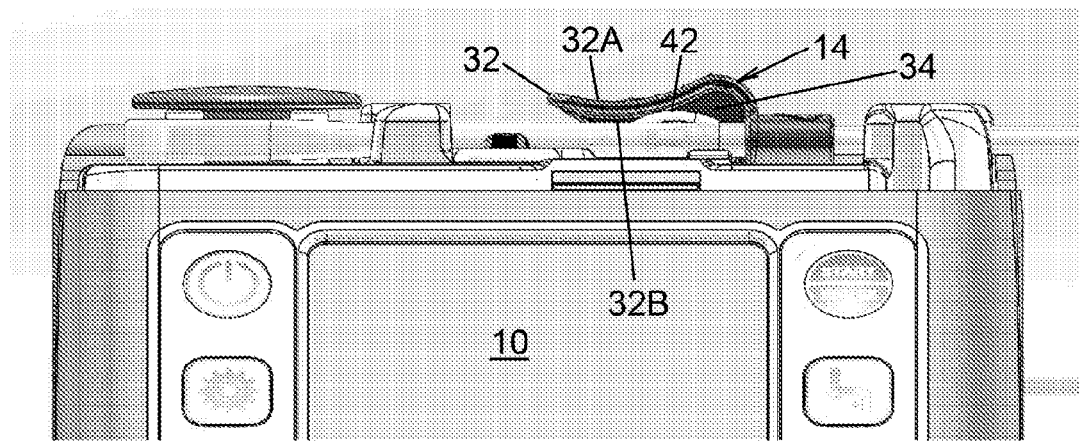
FIG. 5 is an elevational view showing the cassette loaded in the cassette interface.
Figure 6:
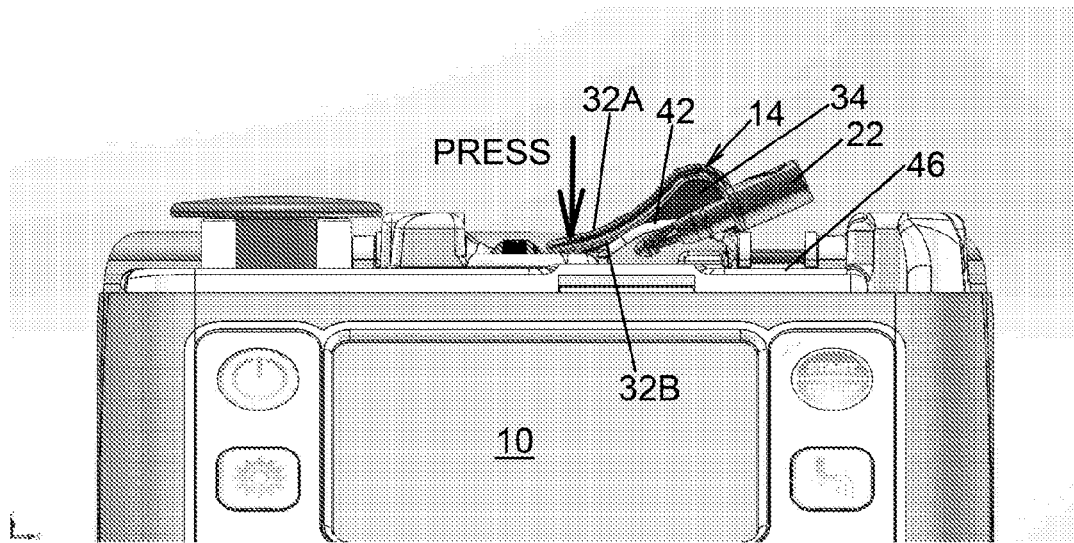
FIG. 6 is a view similar to that of FIG. 5, wherein the cassette is pivoted for easy removal.

As may be understood from FIGS. 1, 5 and 6, when cassette 14 is received by cassette interface 40, the vertical rib 34 of cassette 14 is received in slot 44 of cassette interface 40 and the undersurface 32B of press tab 32 engages a top portion of each of the pair of fulcrum members 42. As shown in the drawings, the undersurface 32B of press tab 32 may be convexly curved in a downward direction and the pair of fulcrum members 42 may be convexly curved in an upward direction. Vertical rib 34 of cassette 14 may be in a central plane of the cassette between the upstream pumping segment connector 18 and the downstream pumping segment connector 20, whereby insertion of rib 34 into slot 44 centers the cassette with respect to the rotational axis of rotor 30.

FIGS. 5 and 6 illustrate an initial step according to the present invention that facilitates removal of cassette 14 from cassette interface 40 of infusion pump 10 (tubing of administration set 12 is omitted in FIG. 5 for clarity). In FIG. 5, cassette 14 is shown in its loaded or installed state, nested in the cassette interface 40. As will be understood from FIG. 6, cassette 14 is pivotable relative to fulcrum members 42 by pressing the press surface 32A of press tab 32. This action assists a user in removing cassette 14 from cassette interface 40 by lifting inflow connector 16 and outflow connector 22 away from base surface 46 of cassette interface 40.

One skilled in the art will recognize that modifications to the depicted embodiment are possible without straying from the invention. For example, press tab may be flat instead of curved, and vertical rib 34 may have an inclined outer edge that is straight instead of curved. Other modifications are also possible. Instead of a pair of fulcrum members 42, only a single, centrally located fulcrum member may be provided as part of cassette interface 40. Under such a modification, cassette 14 may be provided with a pair of laterally-spaced vertical ribs 34 arranged to straddle the single fulcrum member. As another alternative, the undersurface 32B of press tab 32 may include a recess contoured to pivotally receive a top surface of the single fulcrum member. As yet another alternative, the top of the single fulcrum member may include a laterally extending grooved for receiving a rounded, laterally extending rib on undersurface 32B in the manner of a hinge.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the invention.

What is claimed is:

1. A cassette apparatus for an infusion pump, the cassette apparatus comprising:
a cassette for operatively connecting administration set tubing to the infusion pump, the cassette including a press tab having an upwardly facing press surface and an undersurface; and
a cassette interface on the infusion pump for removably receiving the cassette, the cassette interface including at least one fulcrum member;
wherein the undersurface of the press tab engages the at least one fulcrum member when the cassette is received by the cassette interface;
wherein the cassette is pivotable relative to the at least one fulcrum member by pressing the press surface of the press tab to assist in removing the cassette from the cassette interface; and
wherein the cassette interface includes a pair of fulcrum members laterally spaced from one another to define a slot therebetween, and the cassette includes a vertical rib extending downwardly from the undersurface of the press tab, wherein the vertical rib of the cassette is received in the slot of the cassette interface and the undersurface of the press tab engages the pair of fulcrum members when the cassette is received by the cassette interface.

2. The apparatus according to claim 1, wherein the undersurface of the press tab is convexly curved in a downward direction and the pair of fulcrum members are convexly curved in an upward direction.

3. The apparatus according to claim 1, wherein the cassette includes an inflow tubing connector, an outflow tubing connector, an upstream pumping segment connector in flow communication with the inflow tubing connector, and a downstream pumping segment connector in flow communication with the outflow tubing connector.

4. The apparatus according to claim 3, wherein the vertical rib of the cassette is in a central plane of the cassette between the upstream pumping segment connector and the downstream pumping segment connector.

5. The apparatus according to claim 3, wherein the downstream pumping segment connector includes an in-line occluder for restricting flow through the downstream pumping segment connector.

\* \* \* \* \*